(12) United States Patent  
Okamura et al.

(10) Patent No.: US 7,072,104 B2  
(45) Date of Patent: Jul. 4, 2006

(54) OPERATION MICROSCOPE

(75) Inventors: Kazuyuki Okamura, Tokyo (JP); Nobuaki Kitajima, Tokyo (JP)

(73) Assignee: Kabushiki Kaisha Topcon, Tokyo (JP)

( * ) Notice: Subject to any disclaimer, the term of this patent is extended or adjusted under 35 U.S.C. 154(b) by 87 days.

(21) Appl. No.: 10/642,260

(22) Filed: Aug. 18, 2003

(65) Prior Publication Data

US 2004/0085627 A1    May 6, 2004

(30) Foreign Application Priority Data

Aug. 22, 2002 (JP) ............................. 2002-241517  
Jan. 21, 2003 (JP) ............................. 2003-011731

(51) Int. Cl.  
*G02B 21/06* (2006.01)
(52) U.S. Cl. .................................... 359/385; 351/221
(58) Field of Classification Search ............... 359/368, 359/385, 387, 389, 390; 351/205, 221  
See application file for complete search history.

(56) References Cited

U.S. PATENT DOCUMENTS

| | | | | |
|---|---|---|---|---|
| 4,783,159 A | * | 11/1988 | Takagi et al. | 359/377 |
| 4,838,671 A | | 6/1989 | Papritz et al. | 350/516 |
| 5,126,877 A | * | 6/1992 | Biber | 359/389 |
| 5,760,952 A | * | 6/1998 | Koetke | 359/389 |
| 5,856,883 A | * | 1/1999 | Sander | 359/389 |
| 6,011,647 A | * | 1/2000 | Geschwentner | 359/389 |
| 6,483,642 B1 | * | 11/2002 | Deverin | 359/389 |

FOREIGN PATENT DOCUMENTS

| | | |
|---|---|---|
| DE | 40 28 605 A1 | 3/1992 |
| DE | 43 31 635 A1 | 6/1994 |
| EP | 1 083 452 A1 | 3/2001 |
| JP | 7-111507 | 11/1995 |
| JP | 11-169383 | 6/1999 |
| JP | 3008359 | 12/1999 |
| JP | 2002-350735 | 12/2002 |

* cited by examiner

*Primary Examiner*—Mark A. Robinson  
(74) *Attorney, Agent, or Firm*—Armstrong, Kratz, Quintos, Hanson & Brooks, LLP.

(57) ABSTRACT

Provided is an operation microscope capable of obtaining bright and wide range red reflex on an observation image. Further, an operation microscope suitable for an observation of a retina and a vitreous body is provided. A pair of deflection members composed of two deflection mirrors are provided as a deflection means for deflecting illumination light guided from a light source to the vicinity of an optical axis of an observation optical system and guiding it to an eye to be operated through an objective lens. The deflection mirrors are disposed to sandwich the optical axis therebetween and simultaneously guide the illumination lights to the eye to be operated at substantially the same oblique angles with respect to the optical axis from the respective opposite sides. In addition, a stereo variator is made insertable onto the observation optical axis, so that relative positions of optical axes of right and left observation fluxes can be changed.

12 Claims, 9 Drawing Sheets

OPERATION MICROSCOPE

BACKGROUND OF THE INVENTION

1. Field of the Invention

The present invention relates to an operation microscope, more particularly to an ophthalmologic operation microscope.

2. Description of the Related Art

Up to now, various ophthalmologic operations have been conducted. In particular, cataract operation is an example of ophthalmologic operations that have been conducted a large number of times. With respect to cataract operation conducted now, a method called a suction technique is common. The suction technique is a method of cutting the front of the capsule of a crystalline lens along the contour thereof, inserting a suction device from the cut edge, sucking the content of the whitish crystalline lens, and implanting an intraocular lens (IOL) therein in place of the sucked content.

When the suction technique is conducted, an operation microscope is used for obtaining an enlarged observation image of an eye to be operated. At this time, in order to improve the visibility of the observation image, an image of transillumination (red reflex) produced by scattering and reflecting illumination light from the operation microscope on the retina of the eye to be operated is widely utilized. In particular, when the position of the cut edge in the front of the capsule is checked in order to insert the suction device or when it is determined whether or not the content of the crystalline lens is completely sucked, the red reflex is extremely effective.

In order to obtain the red reflex suitable for an operator, various units have been proposed and executed up to now. As main examples of such units, there are "a zero-degree illumination unit" in which a deflection mirror is disposed between the right and left observation optical axes of a binocular visible operation microscope and illumination light is guided to an eye to be operated along the optical axis of an objective lens, and "a complete coaxial illumination unit" in which an illumination optical axis and an observation optical axis are aligned with each other using a half mirror. However, in the zero-degree illumination unit, a region of red reflex resulting from an observation light flux in the right is different from that in the left. Therefore, when binocular vision is conducted, there is a problem in which good fusion of the image is not obtained. In addition, in the complete coaxial illumination unit, because of a reduction in amount of observation light flux resulting from the use of the half mirror, only an entirely dark observation image can be obtained. Therefore, there is a problem in which the visibility is inferior.

Accordingly, in many of the current operation microscopes, a unit called "an angled illumination (oblique illumination) unit" for conducting illumination at a predetermined angle with respect to the optical axis of an observation system (observation optical axis) is widely employed. As a conventional operation microscope in which the angled illumination unit is employed, an operation microscope disclosed in Japanese patent No. 3008359 has been known, for example. In which, the operation microscope includes a deflection mirror for deflecting illumination light emitted from an illumination system toward an eye to be operated, and is constructed such that the deflection mirror can be moved in a direction orthogonal to an observation optical axis to change an angle of the illumination light (hereinafter, referred to as an oblique angle) with respect to the observation optical axis between 0 to 6 degrees, thereby illuminating the eye to be operated.

Also, as another example in which the angled illumination unit is employed, an operation microscope disclosed in Japanese patent laid open No. Hei 11-169383 (FIGS. 2, 4 and 5) includes a prism for deflecting illumination light emitted from an illumination optical system toward an eye to be operated and a shielding disk for blocking a part of the illumination light passing through the prism, and is constructed such that a partial area of the illumination light blocked by the shielding disk is adjusted so as to change an oblique angle with respect to an observation optical axis in the illumination light projected to the eye to be operated by switching the partial area of the illumination light. Note that, as described in the laid open No. Hei 11-169383, the angled illumination unit is generally constructed such that an oblique angle of 2 degrees for obtaining the red reflex and an oblique angle of 6 degrees for obtaining a shadow contrast can be realized. However, in a design for an actual apparatus, the oblique angle particularly for obtaining the red reflex is within a range of about ±0.5 degrees under the present conditions. In the illumination at such an angle is called "approximately coaxial illumination". However, this can be considered as angled illumination with a very small angle.

Now, the operation microscope is generally used for not only anterior eye segment operation such as cataract operation but also for retina and vitreous body operation which is subjected to organs in a deeply inner portion of the eye. The retina and vitreous body operation is generally conducted, while, with a state in which a contact lens is in contact with the retina of the eye to be operated, a light guide (such as a fiber) for intraocular illumination is inserted into the eye and the inner portion of the eye is observed by the operation microscope. At this time, an operator needs to conduct operation while holding the light guide by one hand. Therefore, this becomes a factor that hinders the speed and the accuracy of the operation.

In order to solve such a problem, as in an operation microscope disclosed in Japanese patent laid open No. 2002-350735 (in FIGS. 5 and 10), for example, an operation microscope constructed so as to allow an operator to conduct operation with both hands has been developed. According to the structure of the operation microscope described in such laid open, a front lens is disposed between an object lens and the eye to be operated. An inverter optical element for converting an observation image sensible to the operator as an inverse image by the front lens into an elect image is provided to be insertable onto an observation optical axis. A moving direction in alignment operation by a foot switch is switched in accordance with whether or not the inverter optical element is located on the observation optical axis. In the operation microscope, illumination light is projected from the outside of the eye to be operated thereto in order to observe the inner portion of the eye to be operated through the pupil. As an oblique angle of the illumination light, an angle at which the illumination light can pass through the pupil is used.

Also, a stereoscopic microscope disclosed in Patent publication No. Hei 7-111507 (FIGS. 1 and 2) includes a stereo angle converter for changing an oblique angle of illumination light (optical main body thereof; which is also called a stereo (angle) variator). The stereo angle converter is constructed such that an optical member formed in an inverted V-shape is rotatable on an observation optical axis. The arrangement of the optical member is changed to change a stereo base of right and left axes, thereby adjusting a stereo angle of the observation light. Accordingly, even when the pupil of a patient is small, the retina can be observed.

However, in the operation microscopes using the angled illumination unit, which are described in U.S. Pat. No. 3,008,359 and patent laid open No. Hei 11-169383, the following problem emerges. That is, because an angle is provided between the illumination optical axis and the observation optical axis, a region which is not irradiated with the illumination light is caused within an observable area of the retina, and a part of the red reflex is not incident into the observation optical system. As a result, a region in which the red reflex is not obtained is caused within an observation image.

In order to cope with the problems above, an operation microscope has been proposed in which a deflection mirror for performing the angled illumination is made movable to positions symmetric with respect to an observation optical axis, and the position of the deflection mirror is shifted so as to change a region in which the red reflex can be obtained in the observation image. However, the red reflexes cannot be obtained in the entire observation image at one time. Therefore, the position of the reflection mirror needs to be shifted every time when a region in which the generation of the red reflex is desired is changed during operation, resulting that the operation microscope is not suitable in operability.

On the other hand, when the operation microscope that can be used for the retina and vitreous body operation as described in Japanese patent laid open No. 2002-350735 is used for a patient with a small pupil such as a glaucoma patient, because the observation light is blocked by the pupil, there is a case where observation cannot be sufficiently conducted. In order to avoid such a problem, in the case where the stereo variator or the like is used to narrow the stereo base, when the stereo variator and the deflection mirror are disposed in series as in the stereoscopic microscope described in Japanese patent publication No. Hei 7-111507, the observation light is easily shaded by the deflection mirror. Accordingly, there is the case where the amount of light in the periphery of the observation image becomes insufficient. In some cases, observation becomes impossible.

Also, although there is no problem in the stereoscopic microscope for examination, in the operation microscope, there is a fear that a trouble is caused on an operation because a distance from the eye to be operated to an eyepiece (operating distance) becomes longer. In other words, an operator conducts an operation while peeping through the eyepiece to observe the eye to be operated. Accordingly, the cases can be assumed where the operator has to perform an operation with his arms unnaturally reached out, or the operator's hands do not reach the eye to be operated due to his frame.

SUMMARY OF THE INVENTION

The present invention has been made in view of the above circumferences. Therefore, an object of the present invention is to provide an operation microscope capable of obtaining bright and wide range red reflex on an observation image.

A further object of the present invention is to provide an operation microscope which can be suitably adapted for the anterior eye segment operation as well as the retina and vitreous body operation, in particular, in the case of the latter operation, which is unlikely to cause shading of observation light and which is preferable in operability.

In order to achieve the above-mentioned objects, according to a first aspect of the present invention, there is provided an operation microscope which has: an observation optical system including an objective lens opposed to an eye to be operated; an illumination optical system for guiding illumination light from a light source to a vicinity of an optical axis of the observation optical system; and a deflection means for deflecting the illumination light guided to the vicinity of the optical axis of the observation optical system by the illumination optical system and guiding the illumination light to the eye to be operated through the objective lens, characterized in that the deflection means includes a pair of deflection members which are a first deflection member for guiding a first part of the illumination light at a predetermined oblique angle with respect to the optical axis of the observation optical system and a second deflection member for guiding a second part of the illumination light at an oblique angle substantially equal to the predetermined oblique angle with respect to the optical axis simultaneously with guiding of the first part of the illumination light by the first deflection member, the second deflection member being disposed in an opposite side to the first deflection member so as to sandwich the optical axis of the observation optical system therebetween.

According to the present invention, the operation microscope is operated such that a partial region of an observation image in which red reflex is not obtained from the first part of the illumination light guided by one deflection member of the pair of deflection members is compensated by red reflex obtained from the second part of the illumination light guided by the other deflection member. Therefore, the red reflex over an observable wide range on the retina can be obtained at one time. In addition, the illumination lights are simultaneously guided to the eye to be operated by the pair of deflection members, so that the bright red reflex can be obtained.

Further, according to a second aspect of the present invention there is provided the operation microscope according to the first aspect, characterized in that one deflection member of the pair of deflection members is disposed between the illumination optical system and the optical axis of the observation optical system and the other deflection member is disposed in an opposite side to the one deflection member so as to sandwich the optical axis of the observation optical system therebetween.

According to the present invention, the pair of deflection members are disposed along an optical axis of the illumination optical system. Therefore, the bright and wide range red reflex can be obtained at one time while avoiding a complicated design.

Also, according to a third aspect of the present invention there is provided the operation microscope according to the first aspect or the second aspect, characterized in that each of the pair of deflection members guides the part of the illumination light to the eye to be operated at an oblique angle of 1.5 to 2.5 degrees, preferably, 2 degrees with respect to the optical axis of the observation optical system.

According to the present invention, the bright and wide range red reflex can be obtained at one time within an oblique angle range which is actually used in an available operation microscope.

Further, according to a fourth aspect of the present invention there is provided the operation microscope according to any one of the first to the third aspects, characterized in that the deflection means further includes a third deflection member that guides a third part of the illumination light to the eye to be operated at an oblique angle larger than those for the pair of deflection members with respect to the optical axis of the observation optical system.

According to the present invention, an illumination method of applying a three-dimensional appearance to the observation image, which is useful for cataract operation, can be conducted in addition to obtaining of the red reflex. Therefore, an operation microscope suitable for cataract operation can be provided.

Further, according to a fifth aspect of the present invention there is provided the operation microscope according to the fourth aspect, further including an emitting region adjusting means for adjusting an emitting region of the illumination light from the light source to switch the deflection members each for guiding the part of the illumination light to the eye to be operated, characterized in that any one of the pair of deflection members, the third deflection member, or a combination of one of the pair of deflection members and the third deflection member is selected based on adjustment of the emitting region of the illumination light by the emitting region adjusting means and the part of the illumination light is guided by the selected deflection member.

According to the present invention, an illumination method of obtaining the red reflex and the illumination method of applying the three-dimensional appearance to the observation image can be easily switched, so that an operation microscope which is highly suitable for cataract operation can be provided.

Also, according to a sixth aspect of the present invention, there is provided the operation microscope according to the fifth aspect, in which the emitting region adjusting means comprising of a shielding disk having slots provided on its periphery to form the emitting regions and a shielding disk driving mechanism formed with a control circuit including a stepping motor, a photo sensor and a foot switch.

According to the present invention, an arbitrary selection of the emitting area of the illumination light in accordance with the desired deflection means can be obtained.

Further, according to a seventh aspect of the present invention there is provided the operation microscope according to the fourth aspect or the fifth aspect, characterized in that one deflection member of the pair of deflection members and the third deflection member are integrally formed.

According to the present invention, an operation microscope suitable for cataract operation can be provided while achieving space saving in terms of design and a reduction in manufacturing cost.

Also, according to an eighth aspect of the present invention there is provided the operation microscope according to the first aspect, in which the observation optical system includes a pair of optical systems composed of an optical system for guiding observation light to a left eye of an operator and an optical system for guiding observation light to a right eye thereof, and the operation microscope is characterized by further including an optical axis position changing means for changing relative positions of optical axes of the right and left observation lights guided to the pair of optical systems and a shifting means capable of retreating at least one of the pair of deflection members and locating the optical axis position changing means on optical paths of the right and left observation lights.

According to the present invention, the deflection member is retreated and the optical axis position changing means is disposed on the optical paths of the observation lights. Accordingly, when the retina and the vitreous body of the eye to be operated are observed, shading of the observation light is unlikely to be caused.

Further, according to an ninth aspect of the present invention there is provided the operation microscope according to the eighth aspect, characterized in that the optical axis position changing means is provided near one deflection member of the pair of deflection members and at an opposite position thereto with respect to the optical axis of the observation optical system and the one deflection member and the optical axis position changing means are integrally shifted by the shifting means.

According to the present invention, the optical axis position changing means is provided near the one deflection member and at the opposite position thereto with respect to the observation optical axis and the one deflection member and the optical axis position changing means are integrally shifted by the shifting means. Therefore, the length of an apparatus in the observation optical axis direction does not become too long, so that an operating distance can be suitably kept. In addition, the deflection member and the optical axis position changing means can be shifted by a single shifting means. Accordingly, an apparatus structure does not become too complicated, thereby keeping the cost low.

Further, according to a tenth aspect of the present invention there is provided the operation microscope according to the eighth aspect or the ninth aspect, characterized in that the one deflection member of the pair of deflection members is disposed between the illumination optical system and the optical axes of the right and left observation lights, the other deflection member is disposed in an opposite side to the one deflection member to sandwich the optical axes of the right and left observation lights therebetween, and the shifting means retreats the other deflection member to a one deflection member side and shifts the optical axis position changing means so as to locate the optical axis position changing means on the optical paths of the right and left observation lights.

According to the present invention, the deflection member is removed to an illumination optical system side, that is, in an opposite direction to a location of an operator and it is unnecessary to provide a convex portion or the like as a space for the retreat on an operator's side. Accordingly, satisfactory operability can be kept.

BRIEF DESCRIPTION OF THE DRAWINGS

In the accompanying drawings:

FIGS. 9(A) and 9(B) are schematic views showing a structure of an operation microscope according to Embodiment 3 of the present invention, in which FIG. 9(A) is a side view of the operation microscope and FIG. 9(B) is a front view of the operation microscope;

FIGS. 11(A) and 11(B) schematic views showing a structure of the operation microscope according to Embodiment 3 of the present invention, in which FIG. 11(A) is a side view of the operation microscope and FIG. 11(B) is a front view of the operation microscope.

DETAILED DESCRIPTION OF THE PREFERRED EMBODIMENTS

Hereinafter, embodiments of the present invention will be described in detail with reference to the drawings.

(Embodiment 1)

(Entire and Individual Part structures of Operation Microscope)

Figure 1:
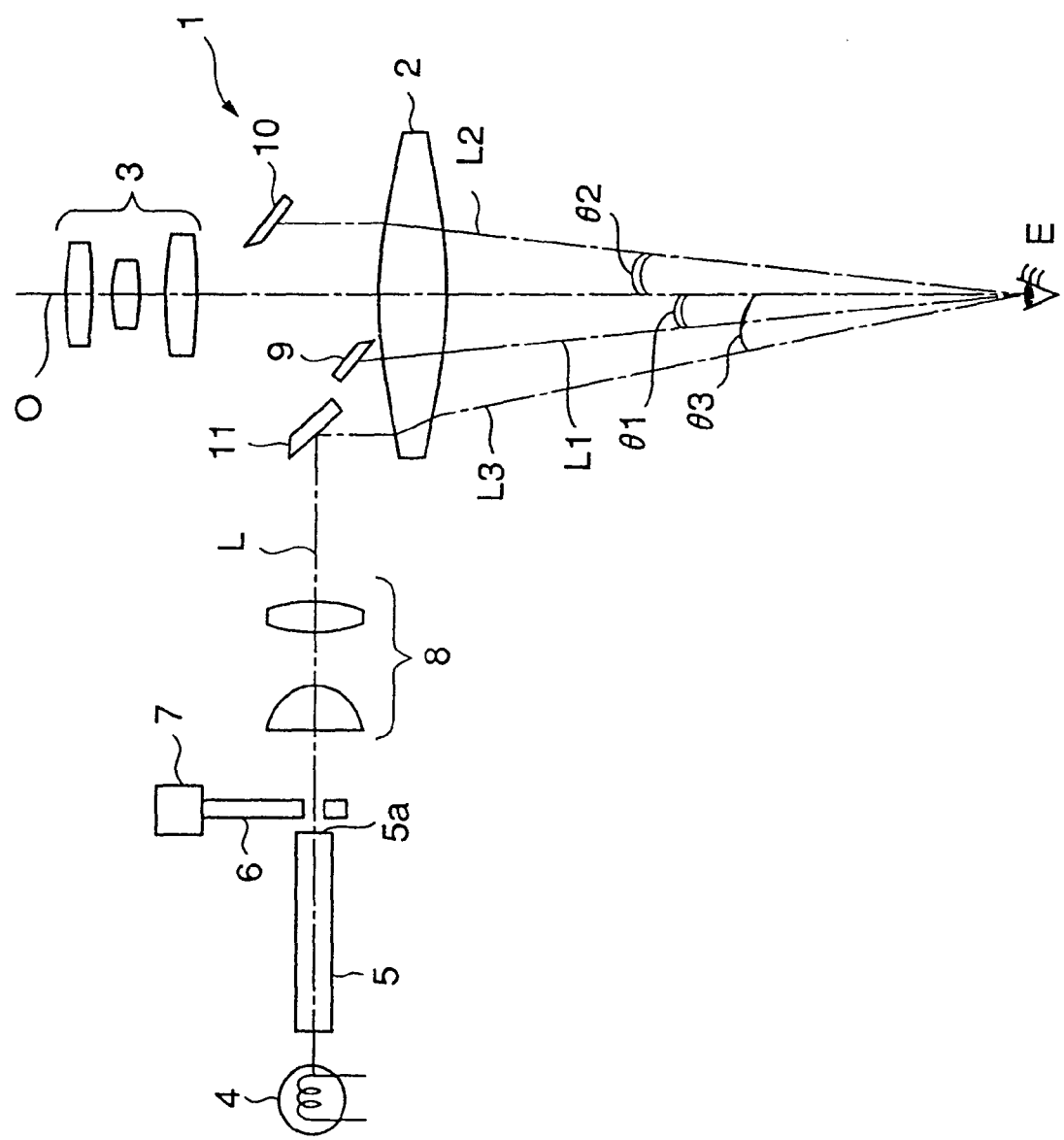
FIG. 1 is a schematic structural view showing an operation microscope according to Embodiment 1 of the present invention.

FIG. 1 shows a schematic structure of an operation microscope 1 according to an embodiment of the present invention. The operation microscope 1 can perform observation with binocular vision and is constructed to include: an objective lens 2 opposed to an eye E of a patient (hereinafter referred to as an eye to be operated) who is undergoing a cataract operation, for example; an eyepiece section (not shown) which is disposed on the extension of the optical axis of the objective lens 2 and provided with left and right eyepieces with which an operator observes the eye to be operated; an observation optical system 3 for guiding an observation light flux to the eyepiece section, which is disposed along the optical axis of the objective lens 2 and composed of a lens group including a variable lens; a light guide 5 for guiding illumination light from a light source 4, which is composed of an optical fiber bundle; a rotatable shielding disk 6, as means for adjusting the emitting region, which is disposed adjacent to an emitting end 5a of the light guide 5 and lets a part of the illumination light emitted from the emitting end 5a; a shielding disk actuating mechanism 7 for controlling rotating operation of the shielding disk 6; an illumination optical system 8, composed of a lens group, for guiding the part of the illumination light passing through slots of the shielding disk 6 to the vicinity of the optical axis "O" of the observation optical system 3 (hereinafter, referred to as an observation optical axis O); and deflection mirrors 9, 10, and 11 as deflection members, disposed near the upper side of the objective lens 2, for reflecting the illumination light guided to the vicinity of the observation optical axis O through the illumination optical system 8 to change the traveling direction of the illumination light to be guided to the eye E to be operated through the objective lens 2.

According to the above-mentioned structure, the illumination light from the light source 4 is blocked by the shielding disk 6 and only a part thereof is guided to illuminate the eye to be operated. However, for the sake of brevity, "the part of the illumination light" passing through the slots of the shielding disk will hereinafter be briefly indicated as "illumination light".

Figure 2:
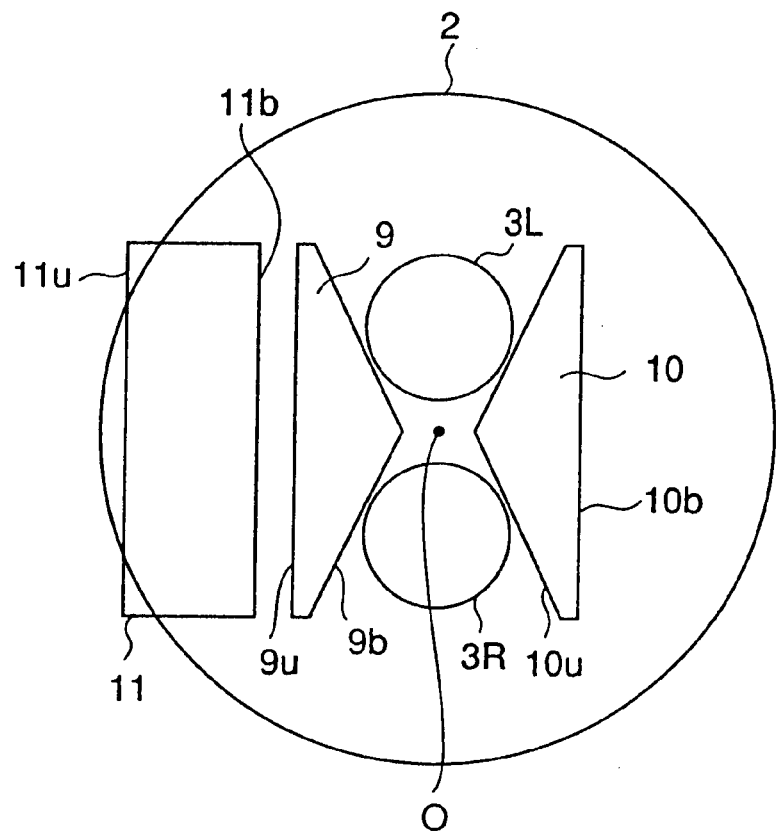
FIG. 2 is a schematic view showing an arrangement of deflection mirrors of the operation microscope according to Embodiment 1 of the present invention.

The observation optical system 3 is composed of the lens group including the objective lens 2. As shown in FIG. 2, the observation optical system 3 has a left observation optical system 3L and a right observation optical system 3R (a pair of optical systems in the present invention). The left observation optical system 3L guides the observation light flux to the left eyepiece of the eyepiece section and the right observation optical system 3R guides the observation light flux to the right eyepiece. Accordingly, the operation microscope 1 can perform binocular vision.

Figure 3:
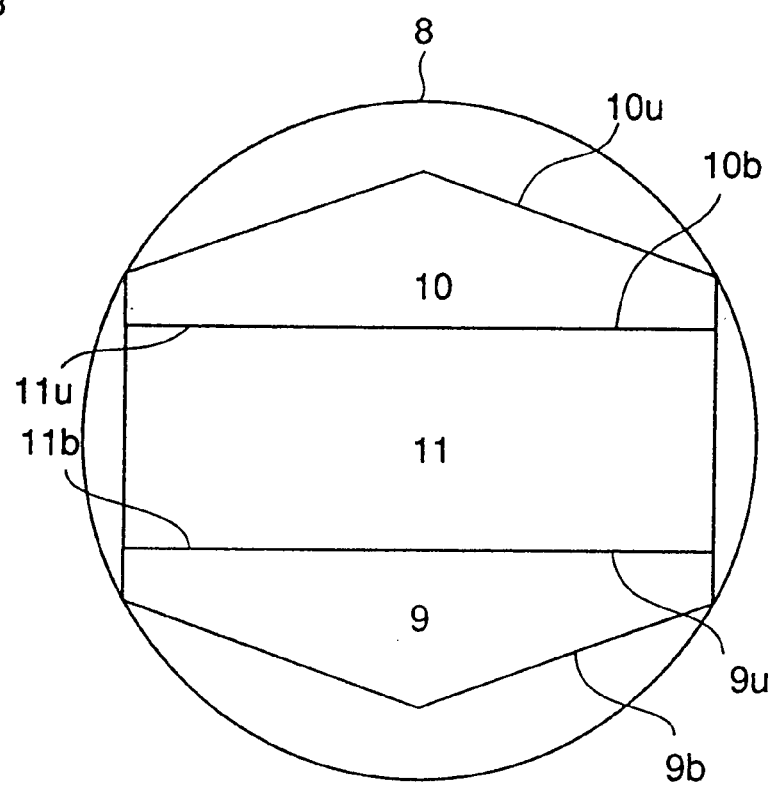
FIG. 3 is a schematic view showing an arrangement of the deflection mirrors of the operation microscope according to Embodiment 1 of the present invention.

Next, an arrangement of the deflection mirrors 9, 10, and 11 will be described with further reference to FIGS. 2 and 3. FIG. 2 shows an arrangement of respective members when the objective lens 2 is viewed from the eye E-to-be-operated side. FIG. 3 shows an arrangement of respective members when an optical axis of the illumination optical system 8 (hereinafter, referred to as an illumination optical axis L) is viewed from the shielding disk 6 side.

As described later, the deflection mirrors 9 and 10 function as a pair of deflection members for simultaneously guiding the illumination light to the eye to be operated. The deflection mirror 9 is disposed between the illumination optical system 8 and the observation optical axis O. The deflection mirror 10 is disposed in an opposite side to the deflection mirror 9 with respect to the observation optical axis O, that is, in a side apart from the illumination optical system 8. Both the deflection mirrors 9 and 10 deflect the illumination lights so as to become parallel to the observation optical axis O. In addition, end portions of the deflection mirrors 9 and 10 that are located closer to the observation optical axis O, more particularly, a lower end 9b of the deflection mirror 9 and an upper end 10u of the deflection mirror 10, are located so that the distances from the observation optical axis O are substantially the same. Therefore, the respective illumination lights deflected by the deflection mirrors 9 and 10 travel in parallel while keeping the same distance from the observation optical axis O, and are refracted by the objective lens 2. Refracted respective illumination lights L1 and L2 illuminate the eye E to be operated at oblique angles $\theta 1$ and $\theta 2$ which are substantially equal to each other with respect to the observation optical axis O.

In this embodiment, the oblique angles $\theta 1$ and $\theta 2$ are set to 2 degrees. However, in an operation microscope used in an actual medical location, an oblique angle of about $2\pm0.5$ degrees is set. Therefore, the oblique angles $\theta 1$ and $\theta 2$ can be set as appropriate in this range.

The lower end 9b of the deflection mirror 9 and the upper end 10u of the deflection mirror 10 each are formed to have a triangular shape so as not to shade the observation light fluxes incident into the left observation optical system 3L and the right observation optical system 3R.

The reflection mirror 11 is disposed closer to the illumination optical system 8 than the deflection mirror 9. An oblique angle $\theta 3$ which is formed between the traveling direction of illumination light L3 deflected by the deflection mirror 11 and the observation optical axis O is set to 6 degrees.

Now, the operation microscope is constructed such that the observation optical axis O indicates a substantially vertical direction. The deflection mirrors 9, 10, and 11 are disposed such that an upper end 9u of the deflection mirror 9 and a lower end 11b of the deflection mirror 11 are located substantially at the same height and a lower end 10b of the deflection mirror 10 and an upper end 11u of the deflection mirror 11 are located substantially at the same height. Therefore, as shown in FIG. 3, when the deflection mirrors are viewed from the illumination optical system 8 side, it looks as if they were disposed in contact with one another. Accordingly, the deflection mirrors 9, 10, and 11 deflect respective separate parts of the illumination light.

Figure 4:
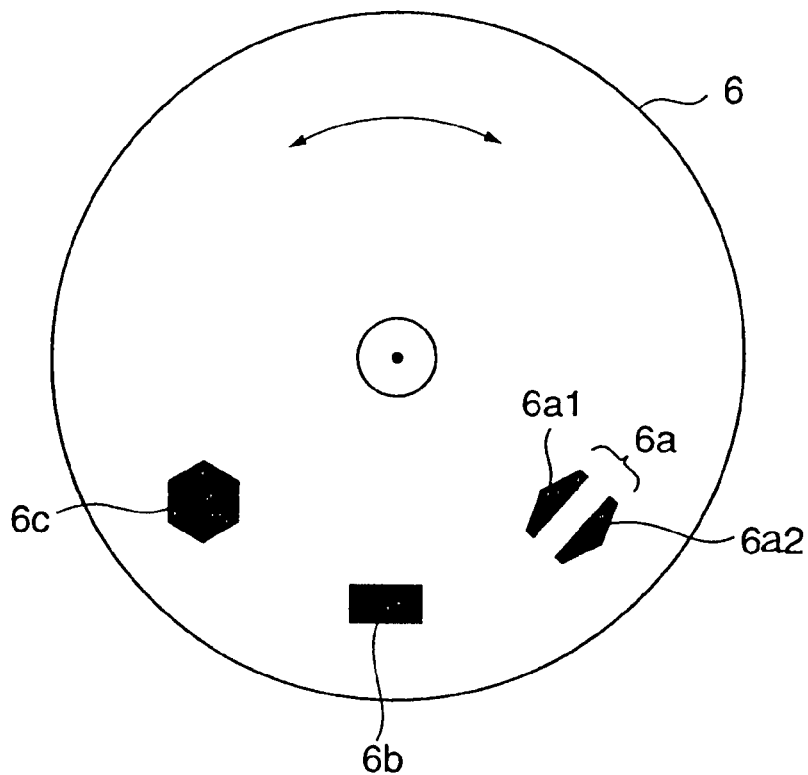
FIG. 4 is a schematic structural view showing a shielding disk of the operation microscope according to Embodiment 1 of the present invention.

The structure of the shielding disk 6 will be described with reference to FIG. 4. The shielding disk 6 is formed in a disk shape and a plurality of slots are formed near the periphery thereof. Although the detail will be described later, the shielding disk 6 is constructed such that the respective slot can be selectively located in its periphery positions facing the emitting end 5a of the light guide 5 by the rotating operation by the shielding disk driving mechanism 7.

With respect to the slots formed in the shielding disk 6, at least three patterns described below are prepared. A first slot is a slot 6a in which two pentagon-shaped slots 6a1 and 6a2 are arranged so that the bottom side portions thereof are opposed to each other. A second slot is a rectangular-shaped slot 6b. A third slot is a hexagon-shaped slot 6c. Of course, the shapes of the slots which can be provided in the shielding disk 6 are not limited to the three types described above. For example, a slot composed of only the slots 6a1 or 6a2 or a slot in which the slot 6a1 or 6a2 and the slot 6b are combined can be provided as appropriate, according to a purpose in illuminating the eye E to be operated.

Figure 5:
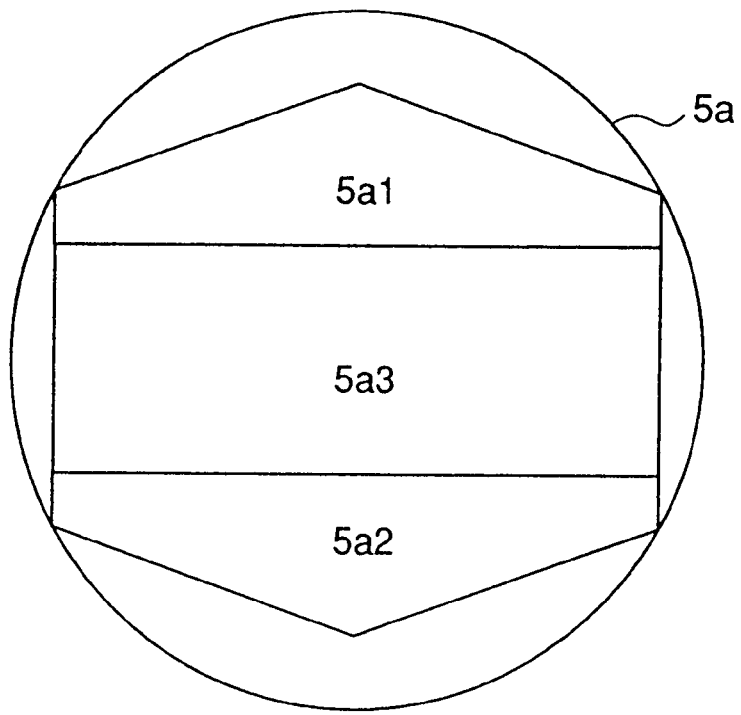
FIG. 5 is a schematic view showing a shielding state of illumination light by the shielding disk of the operation microscope according to Embodiment 1 of the present invention.

FIG. 5 shows a sectional region of the illumination light passing through the slot of the shielding disk 6 when the emitting end 5a of the light guide 5 is viewed through a slot of the shielding disk 6 from the illumination optical system 8 side. A position, a size, and a shape of the slot are designed such that the illumination light passing through the slot is guided to the deflection mirrors 9, 10, and/or 11 through the illumination optical system 8. In other words, the shielding disk 6 blocks a part of the illumination light emitted from the emitting end 5a, which is not guided to the deflection mirrors 9, 10, and/or 11. Note that the illumination light emitted from the light guide 5 becomes an emitting light through slots which will give respective pattern as 5a1, 5a2, 5a3 as shown in solid line of FIG. 5.

When the emitting end 5a of the light guide 5 is covered by the slot 6a, the illumination light having a pattern 5a1 corresponds to the slot 6a1 and the illumination light having a pattern 5a2 corresponds to the slot 6a2 and those are guided respectively to the deflection mirrors 9 and 10. In addition, when the emitting end 5a is covered by the slot 6b, the illumination light having a pattern 5a3 is guided to the deflection mirror 11. Further, when the emitting end 5a is covered by the slot 6c, the illumination light having a pattern obtained by combination of the regions 5a1, 5a2 and 5a3 is guided to each of the deflection mirrors 9, 10 and 11. Note that, because the illumination optical system 8 is constructed as an imaging optical system of odd numbers and correspondence of top and bottom becomes reverse, the slot 6a1 corresponds to the deflection mirror 9 and the slot 6a2 corresponds to the deflection mirror 10. Therefore, when an imaging optical system of even numbers or non-imaging optical system is used, the correspondence of top and bottom becomes good. Thus, it is needless to say that the slot 6a1 corresponds to the deflection mirror 10 and the slot 6a2 corresponds to the deflection mirror 9.

Figure 6:
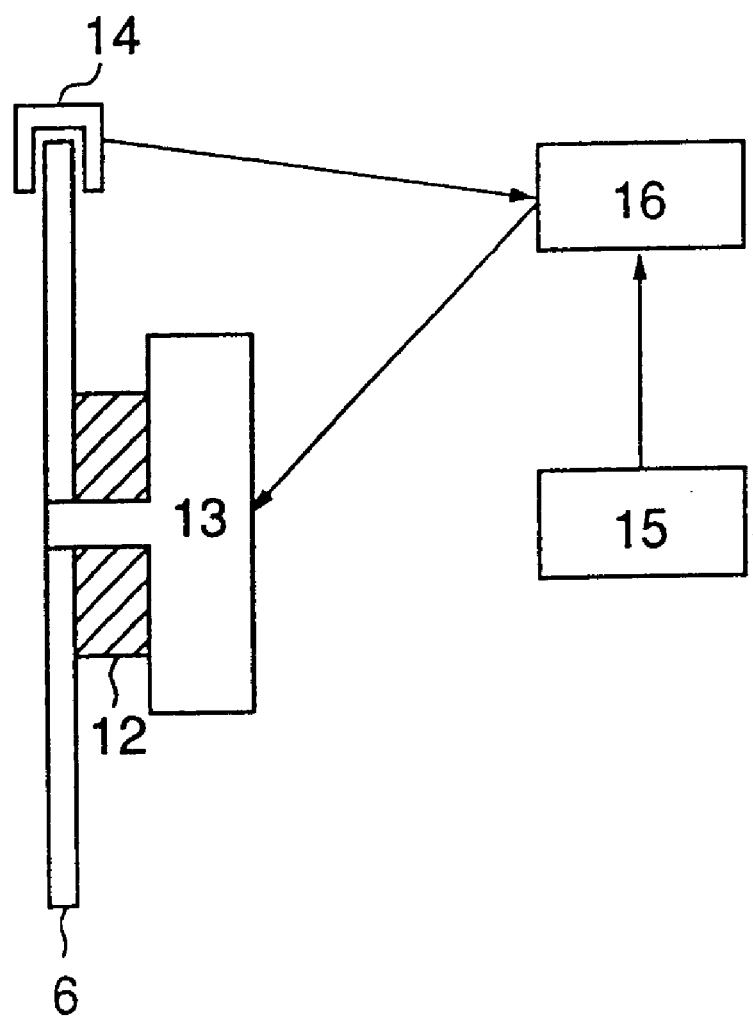
FIG. 6 of a schematic structural view showing a shielding disk driving mechanism of the operation microscope according to Embodiment 1 of the present invention.

FIG. 6 shows a schematic structure of the shielding disk driving mechanism 7. The shielding disk driving mechanism 7 composes an emitting region adjusting means for adjusting an emitting region of illumination light, together with the shielding disk 6. The shielding disk driving mechanism 7 causes the shielding disk 6 to be rotated by using rotating driving force of a stepping motor 13 mounted on the shielding disk 6 through a mount member 12, thereby selectively opposing one of the slots of the shielding disk 6 to the emitting end 5a of the light guide 5. A photo sensor 14, a foot switch 15 and a control circuit 16 are provided to control the drive of the stepping motor 13. The photo sensor 14 is a position detecting unit for detecting a rotational position of the shielding disk 6 and is disposed so as to interpose a portion of the periphery of the shielding disk 6. The foot switch 15 is a control unit for controlling the operation of the stepping motor 13 according to foot operation. The control circuit 16 controls a rotational angle of the stepping motor 13 in accordance with a control signal based on the foot operation of the foot switch 15 and a detection signal which is detected by the photo sensor 14 and based on the rotational position of the shielding disk 6.

Note that, if the rotation axis of the stepping motor 13 and the rotation axis of the shielding disk 6 are located to be made eccentric and a power transmission structure such as a gear structure and a power transmission member such as a timing belt are interposed between the rotation axes so as to transmit the rotation power from the stepping motor 13 to the shielding disk 6, the degree of freedom in arrangement of the stepping motor 13 is increased. In addition to this, distances between the rotation axis and the respective slots in the shielding disk 6 can be shortened regardless of an outer dimension of the stepping motor 13. Therefore, the amount of displacement of the respective slots to the rotational angle of the shielding disk 6 can be reduced and necessary precision with respect to stop positions of the respective slots can be relaxed. Further, a manual knob (not shown) can be mounted to the shielding disk 6 to manually conduct switching operation of the slots.

(Operation of Operation Microscope)

According to the operation microscope 1 of this embodiment which has such a structure, the following observation of the eye to be operated can be conducted.

When red reflex of the eye E to be operated is obtained in cataract operation, for example, the deflection mirrors 9 and 10 are used as a pair of deflection members. As described above, the deflection mirrors 9 and 10 are used to illuminate the eye E to be operated at oblique angles of 2 degrees with respect to the observation optical axis O. In order to obtain the red reflex, first, the foot switch 15 is operated by foot to oppose the slot 6a of the shielding disk 6 to the emitting end 5a of the light guide 5. Illumination light passing through the slot 6a is guided by the illumination optical system 8 and projected to the deflection mirrors 9 and 10. The illumination lights, which are reflected by the deflection mirrors 9 and 10 and deflected in a direction parallel to the observation optical axis O, are each refracted by the objective lens 2 to simultaneously illuminate the eye E to be operated at the oblique angles of 2 degrees with respect to the observation optical axis O. At this time, when the eye E to be operated is given as an origin point, the observation optical axis O is given as a vertical direction axis, and a horizontal direction axis in which a direction toward the light source 4 is a positive direction is set in a direction orthogonal to the observation optical axis O, the eye to be operated is illuminated by the deflection mirror 9 with the oblique angle of +2 degrees with respect to the observation optical axis O and the deflection mirror 10 with the oblique angle of −2 degrees with respect thereto.

Figure 7A:
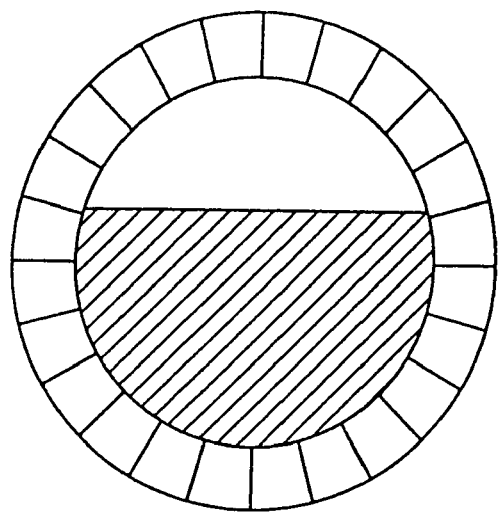
FIGS. 7(A) to 7(C) show types of red reflex obtained by the operation microscope according to Embodiment 1 of the present invention.
Figure 7B:
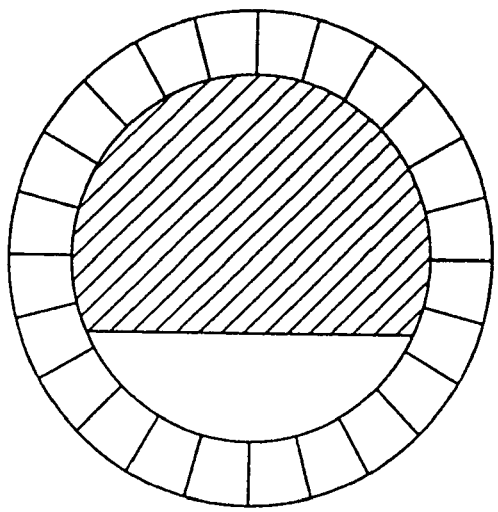
Figure 7C:
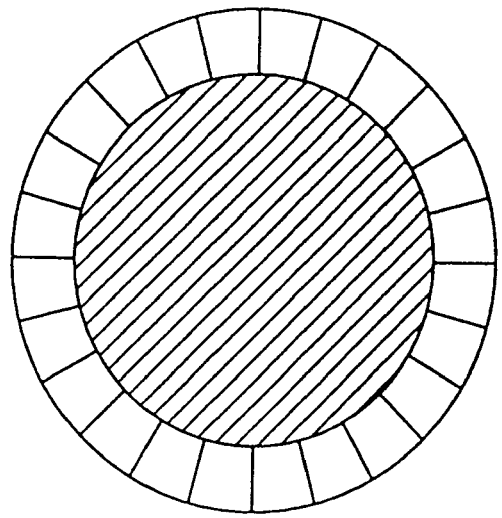

FIGS. 7(A) to 7(C) are schematic views showing states of the red reflexes obtained from the illumination light guided by the deflection mirrors 9 and 10. The red reflexes indicated by hatched areas in the drawings correspond to states obtained at a time when an operator peeps through an eyepiece and visually recognizes the eye E to be operated.

It is assumed that the operator conducts an operation in a location of an opposite side to the light source 4 with respect to the observation optical axis O. A region in each of the drawings, which is located in the periphery and in which lines are radially traced indicates the iris of the eye E to be operated.

FIG. 7(A) shows the red reflex obtained from the illumination light guided by the deflection mirror 9. In the drawing, the contribution of the illumination light resulting from the deflection mirror 10 is neglected for the sake of convenience. The illumination light is incident into the eye E to be operated at the oblique angle of 2 degrees (+2 degrees) in an opposite side to the location side of the operator. Therefore, the operator's side (− direction) on the retina of the eye E to be operated is mainly illuminated and a region in which the red reflex is not obtained is caused in the light source 4 side.

FIG. 7(B) shows the red reflex obtained from the illumination light guided by the deflection mirror 10. In the drawing, the contribution of the illumination light resulting from the deflection mirror 9 is neglected for the sake of convenience. The illumination light has the oblique angle of 2 degrees (−2 degrees) in an opposite side to the side in the case shown in FIG. 7(A). Therefore, the red reflex is obtained in the light source 4 side (+ direction) on the retina of the eye E to be operated.

Note that each of the red reflexes shown in FIGS. 7(A) and 7(B) occupies a region of no less than a half of the retina on an observation image. This indicates a region equivalent to the red reflex obtained by the angle illumination with the general oblique angle of 2 degrees.

FIG. 7(c) shows an observation image of the eye E to be operated which is visually recognized in actuality by the operator. This image is obtained by the combination of the red reflexes obtained from the illumination lights guided by the deflection mirrors 9 and 10 as shown in FIGS. 7(A) and 7(B). As is apparent from the drawing, the red reflex is obtained over the entire observable region on the retina of the eye E to be operated.

Also, a half mirror is not interposed to the operation microscope 1. Accordingly, there is not a reduction in the amount of observation light flux. In addition, the illumination lights guided by the two deflection mirrors 9 and 10 are used, the red reflex obtained therefrom is brighter than the general one.

The deflection mirror 11 is used to conduct an illumination method of applying a three-dimensional appearance to an observation image, which is useful in performing a cataract operation, in addition to the red reflex. First, the foot switch 15 is operated by foot to oppose the slot 6b of the shielding disk 6 to the emitting end 5a of the light guide 5. Illumination light passing through the slot 6b is guided by the illumination optical system 8 and projected to the deflection mirror 11. The illumination light, which is reflected by the deflection mirror 11 and deflected in a direction parallel to the observation optical axis O, is refracted by the objective lens 2 to illuminate the eye E to be operated at the oblique angle of 6 degrees with respect to the observation optical axis O. Accordingly, the three-dimensional appearance is applied to the observation image. Thus, when a suction device is inserted from a cut edge of the front of capsule of a crystalline lens and the content of the whitish crystalline lens is sucked, the suction operation can be conducted without damaging the rear of capsule.

When the foot switch 15 is operated by foot to oppose the slot 6c of the shielding disk 6 to the emitting end 5a of the light guide 5, illumination light passing through the slot 6c is guided by the illumination optical system 8 and projected to all the deflection mirrors 9, 10, and 11 to illuminate the eye E to be operated. According to such an illumination method, a very bright observation image of the eye E to be operated can be visually recognized, with the result that such an image is effectively used to visually recognize a detailed state of the inner portion of the eye E to be operated.

[Embodiment 2]

Figure 8:
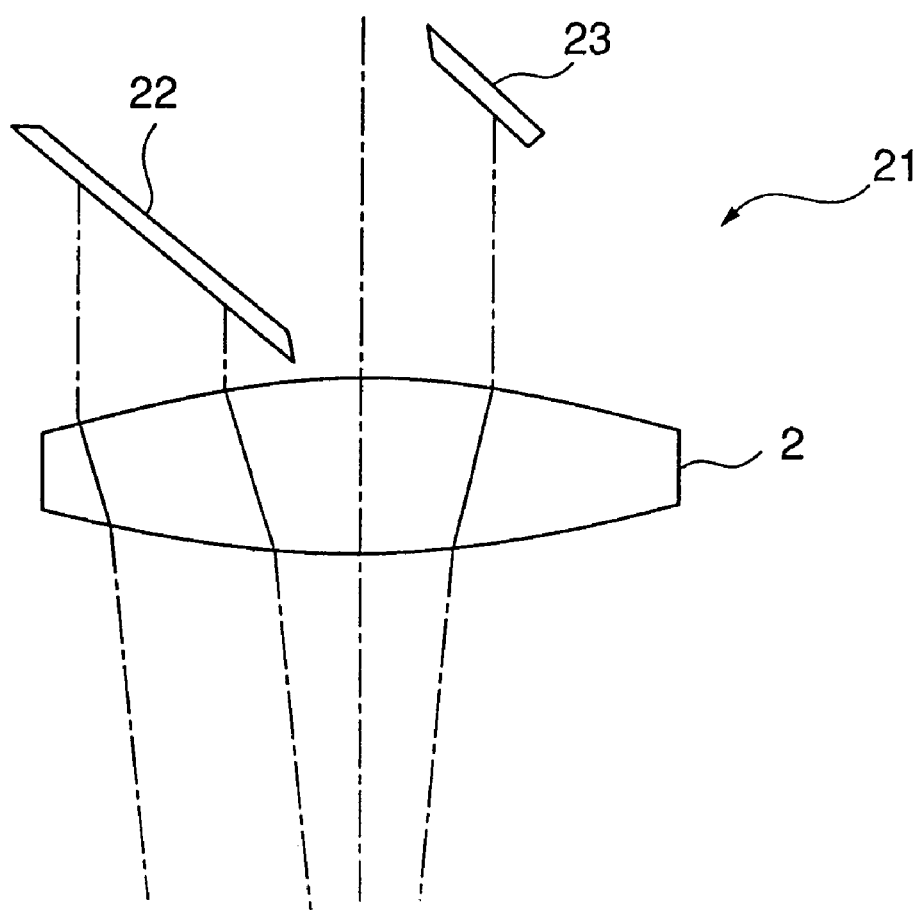
FIG. 8 is a schematic view showing a structure of an operation microscope according to Embodiment 2 of the present invention.

Subsequently, Embodiment 2 of the present invention will be described with reference to the drawing. Embodiment 2 of the present invention is obtained by modifying a part of Embodiment 1 which is described above in detail. FIG. 8 shows a structure of a deflection mirror as a modified part. Note that the same reference symbols as in the description of the operation microscope 1 of Embodiment 1 are used for parts that are not modified.

As shown in FIG. 8, an operation microscope 21 according to Embodiment 2 is obtained by integrally forming the deflection mirrors 9 and 11 described in Embodiment 1. When such integral formation is made, the number of deflection mirrors can be reduced, so that space saving and a reduction in manufacturing cost can be achieved.

The operation microscope 21 includes a deflection mirror 22 disposed between the illumination optical system 8 and the observation optical axis O and a deflection mirror 23 disposed in an opposite side to the deflection mirror 22 with respect to the observation optical axis O, by which an eye E to be operated is illuminated with illumination lights from different directions. The deflection mirror 22 has oblique angles of 2 degrees and 6 degrees with respect to the observation optical axis O and has a size large enough to illuminate the eye E to be operated. In other words, when the illumination light is deflected by a region of the deflection mirror 22 in the observation optical axis O side, the deflection mirror 22 has a size large enough to realize the oblique angle of 2 degrees. When the illumination light is deflected by a region of the deflection mirror 22 on a side apart from the observation optical axis O, the deflection mirror 22 has a size large enough to realize the oblique angle of 6 degrees. On the other hand, the deflection mirror 23 is disposed so as to illuminate the eye E to be operated at a predetermined oblique angle (2 degrees) with respect to the observation optical axis O.

When the slot 6a of the shielding disk 6 is opposed to the emitting end 5a of the light guide 5, illumination light is projected to the region of the deflection mirror 22 in the observation optical axis O side and the deflection mirror 23 and deflected by the deflection mirror 22 in a direction parallel to the observation optical axis O. The deflected illumination lights are refracted by the objective lens to illuminate the eye E to be operated at the respective oblique angles of 2 degrees. Accordingly, the bright and wide range red reflex as shown in FIG. 7(C) can be obtained.

Further, when the slot 6b of the shielding disk 6 is opposed to the emitting end 5a of the light guide 5, illumination light is projected to the region on the side apart from the observation optical axis O of the deflection mirror 22 and deflected by the deflection mirror 22 in a direction parallel to the observation optical axis O. The deflected illumination lights are refracted by the objective lens to illuminate the eye E to be operated at the respective oblique angles of 6 degrees. Accordingly, there is obtained an observation image of the eye E to be operated having a three-dimensional appearance.

Further, when the slot 6b of the shielding disk 6 is opposed to the emitting end 5a of the light guide 5, illumination light is projected to the entire region of the deflection mirror 22 and the deflection mirror 23 and deflected by the deflection mirrors 22 and 23 in a direction parallel to the observation optical axis O. The deflected illumination lights are refracted by the objective lens to illuminate the eye E to be operated. Accordingly, it becomes possible to visually recognize an extremely bright observation image of the eye E to be operated.

As described above, when the slots of the shielding disk 6 are switched, the region of the deflection mirror 22 to which the illumination light is projected can be changed, so that the oblique angles with respect to the illumination light guided by the deflection mirror 22 are switched between 2 degrees and 6 degrees. In addition, when the oblique angle with respect to the illumination light guided by the deflection mirror 22 is switched to 2 degrees, as described in the case where the slot 6a of the shielding disk 6 is selected, the illumination light is also projected to the deflection mirror 23. Therefore, the deflection mirrors 22 and 23 simultaneously guide the illumination lights to the eye E to be operated.

Note that, although the shielding disk 6 is correspondingly applied in description of Embodiment 2, detailed design matters such as positions and sizes of the slots of the shielding disk 6 are slightly different from those of the shielding disk 6 in the description of Embodiment 1. However, because schematic matters such as positions and sizes of the slots are the same, the shielding disk 6 is correspondingly applied.

In the two embodiments described above, the operation microscope suitable to cataract operation is described. Even when the operation microscope of the present invention is used for other ophthalmologic operation, there is no problem. Accordingly, when the operation microscope of the present invention is used for other ophthalmologic operation, it is needless to say that the positions of the deflection mirrors can be adjusted so that the oblique angles suitable for the operation can be adopted as appropriate.

[Embodiment 3]

Figure 9A:
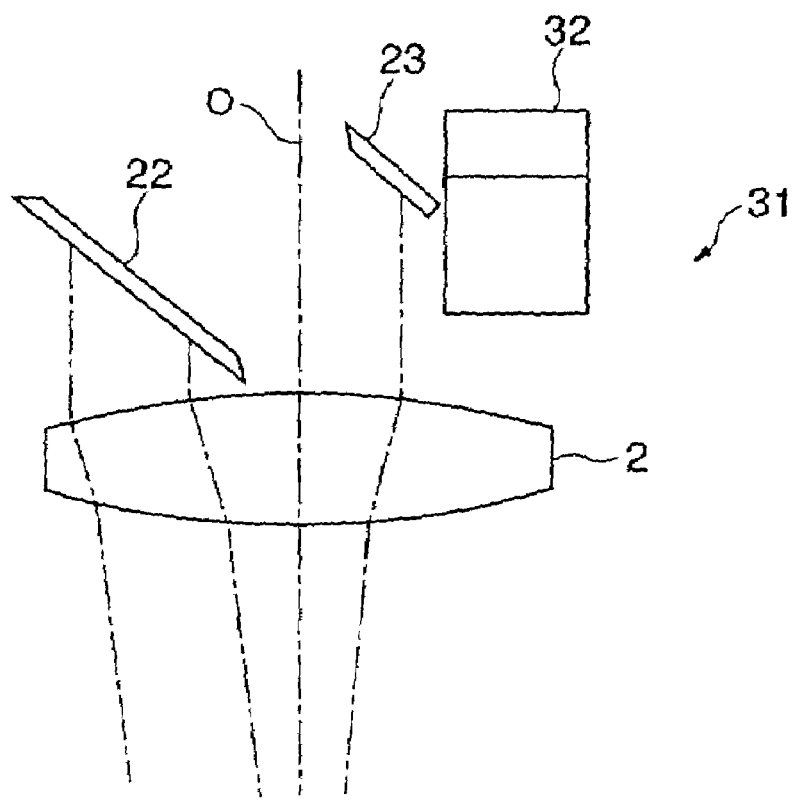
Figure 9B:
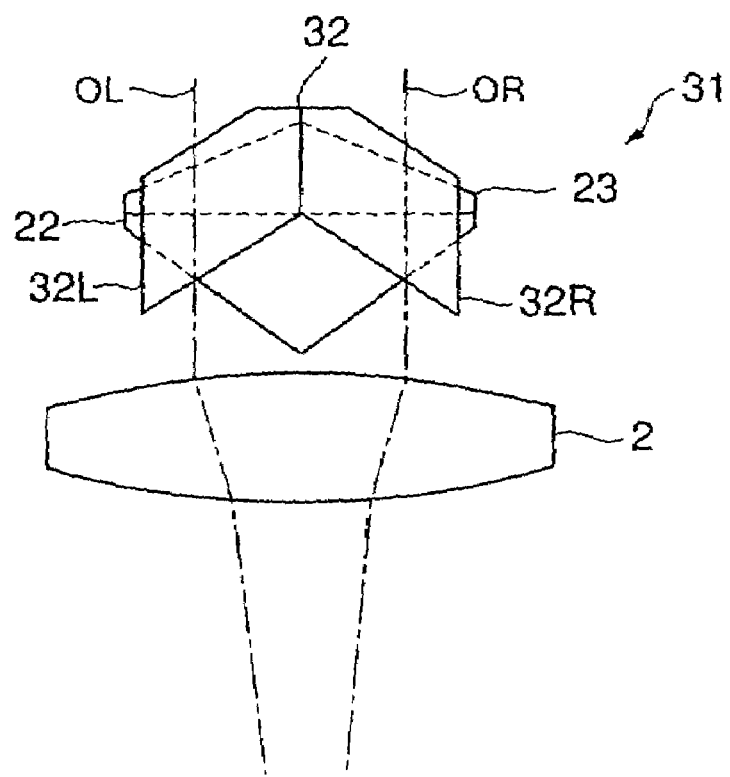

In Embodiment 3 of the present invention, a function is added to the above-mentioned operation microscope, thus structuring an operation microscope preferably usable in not only anterior eye segment operation such as cataract operation in which the red reflex is effectively used but also in retina and vitreous body operation for treating further inner organs such as a retina and a vitreous body. FIGS. 9(A) and 9(B) show a schematic structure of an example of such an operation microscope. Here, FIG. 9(A) is a side view of the operation microscope and FIG. 9(B) is a front view thereof. An operator who conducts an operation is located in the right side in FIG. 9(A). FIG. 9(B) is a view when the operation microscope is viewed from the operator's side. In addition, reference symbols provided in Embodiment 1 are correspondingly applied to portions in Embodiment 3, which have the same structure as the operation microscope of Embodiment 1.

An operation microscope 31 shown in FIGS. 9(A) and 9(B) is constructed by adding to the operation microscope 21 of Embodiment 2 as shown in FIG. 8 a member indicated by reference numeral 32 and a means for shifting the member and the like, which is described below. As is apparent from FIG. 9(A), the operation microscope 31 includes the deflection mirror 22 disposed between the illumination optical system 8 and the observation optical axis O and the deflection mirror 23 disposed in the opposite side to the deflection mirror 22 with respect to the observation optical axis O, by which the eye E to be operated can be illuminated with illumination lights from different directions. Further, a stereo variator 32 as an optical axis position changing means in the present invention is disposed near the deflection mirror 23 and in the opposite side thereof with respect to the observation optical axis O. Although not shown in both drawings, the deflection mirror 23 and the stereo variator 32 are integrally connected with each other through, for example, a connection member to compose a unit. Assume that the observation optical axis O means a left observation optical axis OL and a right observation optical axis OR as shown in FIG. 9(B) for the sake of convenience. The left observation optical axis OL and the right observation optical axis OR indicate the optical axes of the observation light fluxes guided to the left observation optical system 3L and the right observation optical system 3R.

Also, as shown in FIG. 9(B), the stereo variator 32 is obtained by combining optical members 32L and 32R each having two parallel surfaces. The two parallel surfaces of the optical member 32L are tilted at a predetermined angle with respect to the left observation optical axis OL. In addition, the two parallel surfaces of the optical member 32R are tilted at a predetermined angle with respect to the right observation optical axis OR. Accordingly, when the stereo variator 32 is disposed such that the optical members 32L and 32R are located on the left observation optical axis OL and the right observation optical axis OR, respectively, relative positions of the left observation optical axis OL and the right observation optical axis OR can be changed.

Figure 10:
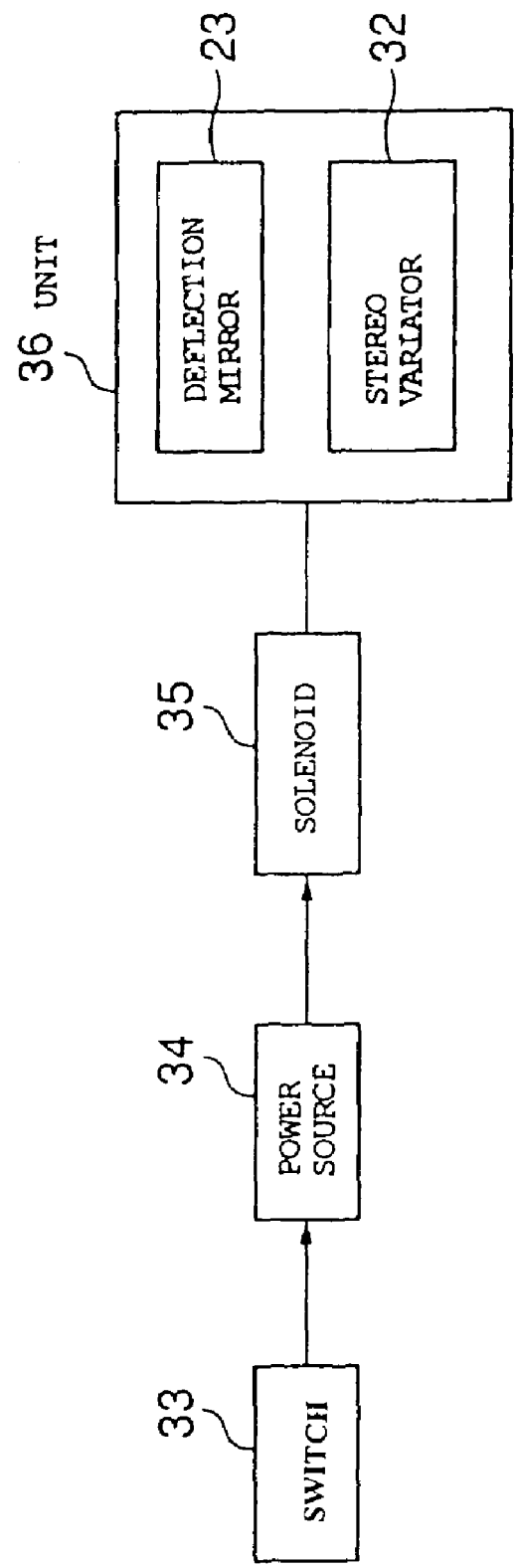
FIG. 10 is a block diagram showing a structure of the operation microscope according to Embodiment 3 of the present invention.

Subsequently, a shifting means for shifting the stereo variator 32 will be described with reference to FIG. 10 which is a block diagram of its structure. The shifting means is constructed to include a switch 33, a power source 34, and a solenoid 35. The switch 33 is a changing switch for changing the position of the unit 36 described above including the deflection mirror 23 and the stereo variator 32, and located at a position which an operator can easily reach, for example, a lens barrel storing respective optical systems. In addition, when the operation microscope 31 is provided with a foot switch, the position of the unit 36 may be changed using the foot switch. Alternatively, the switch 33 may be located in the foot switch. The power source 34 applies a voltage to the solenoid 35 corresponding to switching of the switch 33. The solenoid 35 is composed of, for example, a plunger type linear electromagnetic solenoid (LES). When the voltage is applied from the power source 34, the solenoid is operated and moves the unit 36.

Figure 11A:
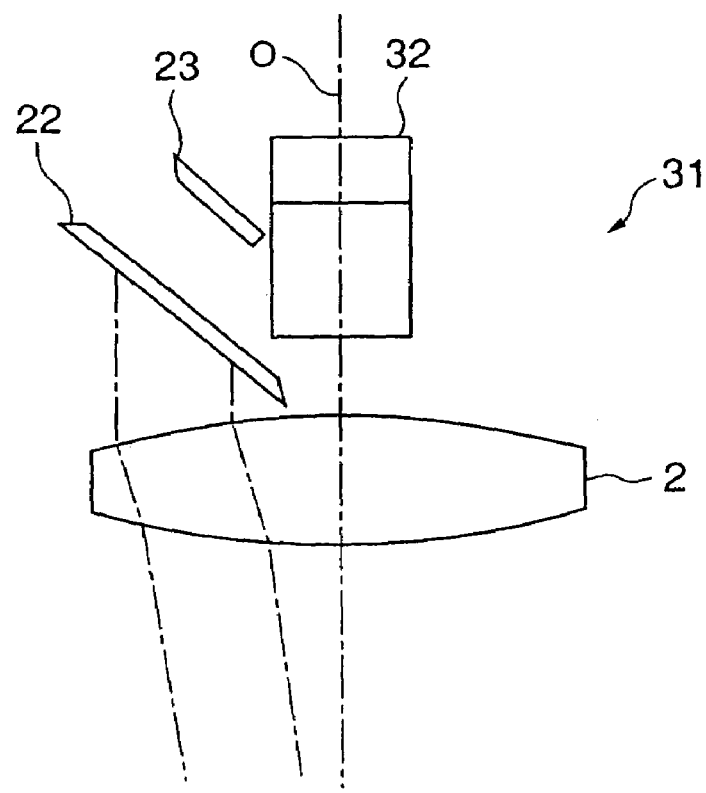
Figure 11B:
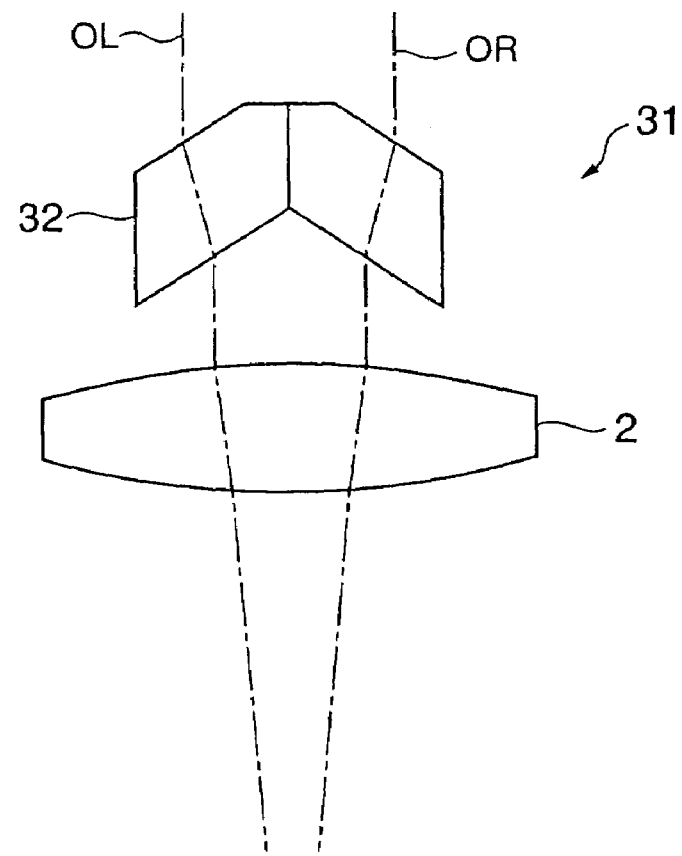

FIGS. 11(A) and 11(B) show a state at a time when the unit 36 is shifted on the observation optical axis O by the above-mentioned shifting means. FIG. 11(A) is a side view of the operation microscope 31 in such a state and FIG. 11(B) is a front view when the operation microscope is viewed from the operator's side. Note that, in order to clearly show the operation of the stereo variator 32, the deflection mirrors 22 and 23 are omitted in FIG. 11(B).

In FIG. 11(A), the stereo variator 32 is disposed on the observation optical axis O. In addition, the deflection mirror 23 is removed to the deflection mirror 22 side, that is, the observation optical system 8 side. On the other hand, in FIG. 11(B), the position of the left observation optical axis OL and that of the right observation optical axis OR are changed by the optical members 32L and 32R, respectively, and a relative distance therebetween becomes smaller as compared with the state shown in FIG. 9(B).

Note that, when the switch 33 is switched to the opposite side, the unit 36, that is, the deflection mirror 23 and the stereo variator 32 are shifted from the position shown in FIGS. 11(A) and 11B to the original position shown in FIGS. 9(A) and 9(B). Therefore, when the operator operates the switch 33, the position of the deflection mirror 23 and that of the stereo variator 32 can be changed appropriately.

On the other hand, in the operation microscope 31 of Embodiment 3 of the present invention as described above, the deflection mirror 23 and the stereo variator 32 are not necessarily shifted as the integral unit 36, but it may be constructed so that shifting means is provided for each of the deflection mirror 23 and the stereo variator 32 to move them separately.

Also, a design with respect to the arrangement of the stereo variator 32 and the shifting directions (removal directions) of the deflection mirror 23 and the stereo variator 32 can be changed appropriately according to purposes.

Further, it is needless to say that the above-mentioned structure may be added to the operation microscope 1 of Embodiment 1. Even in that case, the slot 6b of the shielding disk 6 is disposed on an illumination optical axis L and the illumination light is made incident into the eye E to be operated using the deflection mirror 11.

Now, the reason why the operation microscope is constructed so as to use the deflection mirror 23 and the stereo variator 32 alternatively is because functions required for the anterior eye segment operation and the retina and vitreous body operation are different. In other words, the red reflex is effectively used in the anterior eye segment operation but it is unnecessary to observe a retina and a vitreous body which are located in a further deeper portion of the eye to be operated. On the other hand, it is essential to observe the retina and the vitreous body in the retina and vitreous body operation but there is no chance to use the red reflex. In addition, the operation microscope 31 of the present invention can be applied to the retina and vitreous body operation using either a method of inserting a light guide for illumination into the eye and illuminating it therethrough or a method of illuminating the eye with illumination light from the outside.

As described above, when the operation microscope 31 is constructed so that the position of the unit 36 can be changed, it becomes suitable for both the anterior eye segment operation and the retina and vitreous body operation. In other words, in the anterior eye segment operation, when the stereo variator 32 is used while being removed from the observation optical axis O as shown in FIGS. 9(A) and 9(B), preferable red reflex can be produced. On the other hand, in the retina and vitreous body operation, when the stereo variator 32 is inserted onto the observation optical axis O and the slot 6b of the shielding disk is applied for illumination, the retina and the vitreous body of the eye E to be operated can be clearly observed.

Here, when the retina and vitreous body operation is conducted, the reason why the illumination light obtained by selecting the slot 6b from various slots provided in the shielding disk 6 is used is as follows. A pupil P as a region into which the illumination light flux is made incident and from which the observation light flux is emitted is an extremely small region. When an incident position of the illumination light flux and an emitting position of the observation light flux are overlapped with or close to each other within the small region, there is a case where reflected light of the illumination light flux on the cornea is mixed into the observation light flux, thereby reducing the image quality of an observation image. In order to avoid such a problem, it is required that the incident position of the illumination light flux and the emitting position of the observation light flux are sufficiently separated from each other so that the cornea reflected light of the illumination light flux does not affect the observation light flux. Taking this fact into consideration, the illumination light flux obtained by applying the slot 6b is deflected at a position of the deflection mirror 22 which is maximally apart from the observation optical axis O and incident into the eye E to be operated at a large oblique angle with respect to the observation optical axis O. Therefore, the incident position of the illumination light flux and the emitting position of the observation light flux can be further separated from each other, so that the above-mentioned problem can be solved.

Also, the operation microscope 31 is constructed such that the stereo variator 32 is inserted onto the observation optical axis O and simultaneously the deflection mirror 23 is retreated therefrom. Accordingly, shading of the observation light flux by the deflection mirror 23 is prevented, so that there is no case where the periphery of the observation image becomes dark making observation impossible. Note that a structure in which the deflection mirror 22 is retreated may be further added.

Further, the operation microscope 31 is constructed so as to shift the deflection mirror 23 and the stereo variator 32 in a direction orthogonal to the observation optical axis O. Therefore, there is no case where the length of an apparatus in the observation optical axis O direction becomes too long. Thus, a distance between the eye E to be operated and the eyepiece section (operating distance) can be suitably kept.

Also, the operation microscope 31 is constructed so as to retreat the deflection mirror 23 toward the illumination optical system 8 side. Accordingly, because it is unnecessary to provide a retreated space in the operator's side of the lens barrel, there is no case where the operation is interrupted. Thus, the operability is kept.

Various operation microscopes described above in detail are solely examples of the embodiments and the present invention is not limited to the embodiments.

According to the present invention, there is provided an operation microscope capable of obtaining bright and wide range red reflex on an observation image.

Also, according to the present invention, an operation microscope capable of obtaining the above-mentioned wide range red reflex on the entire observable region of the retina of the eye to be operated can be provided.

Further, according to the present invention, an operation microscope capable of obtaining the bright and wide range red reflex on an observation image can be provided while achieving space saving and a reduction in cost.

Furthermore, according to the present invention, an operation microscope capable of being suitably adopted for use in both the anterior eye segment operation and the retina and vitreous body operation can be provided. In particular, in the case of the retina and vitreous body operation, shading of the observation light is unlikely to be caused and satisfactory operability is also kept.

What is claimed is:

1. An operation microscope comprising:
    an observation optical system including an objective lens opposed to an eye to be operated;
    an illumination optical system for guiding illumination light from a light source to a vicinity of an optical axis of the observation optical system; and
    a deflection means for deflecting the illumination light guided to the vicinity of the optical axis of the observation optical system by the illumination optical system and guiding the illumination light to the eye to be operated through the objective lens,
    wherein the deflection means includes a pair of deflection members which are a first deflection member for guiding a first part of the illumination light at a predetermined oblique angle with respect to the optical axis of the observation optical system and a second deflection member for guiding a second part of the illumination light at an oblique angle substantially equal to the predetermined oblique angle with respect to the optical axis simultaneously with guiding of the first part of the illumination light by the first deflection member, the second deflection member being disposed in an opposite side to the first deflection member so as to sandwich the optical axis of the observation optical system therebetween, wherein the deflection means further includes a third deflection member that guides a third part of the illumination light to the eye to be operated at an oblique angle larger than those for the pair of deflection members with respect to the optical axis of the observation optical system, the operation microscope further comprising:

an emitting region adjusting means for adjusting an emitting region of the illumination light from the light source selected from one of the 1st, 2nd, and 3rd or plural deflection members by switching one part of the illumination light so as to cope with the shape of the deflection members to be guided to the eye to be operated.

2. An operation microscope according to claim 1, wherein one deflection member of the pair of deflection members is disposed between the illumination optical system and the optical axis of the observation optical system and the other deflection member is disposed in an opposite side to the one deflection member so as to sandwich the optical axis of the observation optical system therebetween.

3. An operation microscope according to claim 2, wherein each of the pair of deflection members guides the part of the illumination light to the eye to be operated at an oblique angle of 1.5 to 2.5 degrees with respect to the optical axis of the observation optical system.

4. An operation microscope according to claim 1 or 2, wherein one deflection member of the pair of deflection members and the third deflection member are integrally formed.

5. An operation microscope according to claim 3, wherein the predetermined oblique angle is 2 degrees.

6. An operation microscope according to claim 1, wherein the observation optical system includes a pair of optical systems composed of an optical system for guiding observation light to a left eye of an operator and an optical system for guiding observation light to a right eye thereof, the operation microscope further comprising: an optical axis position changing means for changing relative positions of optical axes of the right and left observation lights guided to the pair of optical systems; and a shifting means capable of retreating at least one of the pair of deflection members and locating the optical axis position changing means on optical paths of the right and left observation lights.

7. An operation microscope according to claim 6, wherein the optical axis position changing means is provided near one deflection member of the pair of deflection members and at an opposite position thereto with respect to the optical axis of the observation optical system, and wherein the one deflection member and the optical axis position changing means are integrally shifted by the shifting means.

8. An operation microscope according to claim 6 or 7, wherein the one deflection member of the pair of deflection members is disposed between the illumination optical system and the optical axes of the right and left observation lights, the other deflection member is disposed in an opposite side to the one deflection member to sandwich the optical axes of the right and left observation lights therebetween, and wherein the shifting means retreats the other deflection member to one deflection member side and shifts the optical axis position changing means so as to locate the optical axis position changing means on the optical paths of the right and left observation lights.

9. An operation microscope comprising:

an observation optical system including an objective lens opposed to an eye to be operated;

an illumination optical system for guiding illumination light from a light source to a vicinity of an optical axis of the observation optical system; and a deflection means for deflecting the illumination light guided to the vicinity of the optical axis of the observation optical system by the illumination optical system and guiding the illumination light to the eye to be operated through the objective lens, wherein the deflection means includes a pair of deflection members which are a first deflection member for guiding a first part of the illumination light at a predetermined oblique angle with respect to the optical axis of the observation optical system and a second deflection member for guiding a second part of the illumination light at an oblique angle substantially equal to the predetermined oblique angle with respect to the optical axis simultaneously with guiding of the first part of the illumination light by the first deflection member, the second deflection member being disposed in an opposite side to the first deflection member so as to sandwich the optical axis of the observation optical system therebetween, wherein the deflection means further includes a third deflection member that guides a third part of the illumination light to the eye to be operated at an oblique angle larger than those for the pair of deflection members with respect to the optical axis of the observation optical system, the operation microscope further comprising:

an emitting region adjusting means for adjusting an emitting region of the illumination light from the light source to switch the shield disk to guide the part of the illumination light to the eye to be operated, wherein any one of the pair of deflection members, the third deflection member, or a combination of one of the pair of deflection members and the third deflection member is selected based on adjustment of the emitting region of the illumination light by the emitting region adjusting means and the part of the illumination light is guided by the selected deflection member to the eye to be operated.

10. An operation microscope according to claim 9, wherein the emitting region adjusting means comprises of a shielding disk having slots provided on its periphery to form the emitting regions and shielding disk driving mechanism formed with a control circuit including a stepping motor, a photo sensor and a foot switch.

11. An operation microscope, comprising:

an observation optical system including an objective lens opposed to an eye to be operated;

an illumination optical system for guiding illumination light from a light source to a vicinity of an optical axis of the observation optical system; and a deflection means for deflecting the illumination light guided to the vicinity of the optical axis of the observation optical system by the illumination optical system and guiding the illumination light to the eye to be operated through the objective lens, wherein the deflection means includes a pair of deflection members which are a first deflection member for guiding a first part of the illumination light at a predetermined oblique angle with respect to the optical axis of the observation optical system and a second deflection member for guiding a second part of the illumination light at an oblique angle substantially equal to the predetermined oblique angle with respect to the optical axis simultaneously with guiding of the first part of the illumination light by the first deflection member, the second deflection member being disposed in an opposite side to the first deflection member so as to sandwich the optical axis of the observation optical system therebetween, wherein the deflection means further includes a third deflection member that guides a third part of the illumination light to the eye to be operated at an oblique angle larger than those for the pair of deflection members with respect to the optical axis of the observation optical system, the operation microscope further comprising:

an emitting region adjusting means for adjusting an emitting region of the illumination light from the light source to switch the deflection members so as to cope with the shape of the deflection members each guiding the part of the illumination light to the eye to be operated, wherein any one of the pair of deflection members, the third deflection member, or a combination of one of the pair of deflection members and the third deflection member is selected based on adjustment of the emitting region of the illumination light by the emitting region adjusting means and the part of the illumination light is guided by the selected deflection member.

12. An operation microscope according to claim 11, wherein the emitting region adjusting means comprises of a shielding disk having slots provided on its periphery to form the emitting regions and shielding disk driving mechanism formed with a control circuit including a stepping motor, a photo sensor and a foot switch.

* * * * *